United States Patent [19]

Forman et al.

[11] Patent Number: 5,275,608
[45] Date of Patent: Jan. 4, 1994

[54] GENERIC ENDOSCOPIC INSTRUMENT

[75] Inventors: Jeffrey L. Forman, Bronx, N.Y.; Fredric L. Milder, Brookline, Mass.; Henri F. deGuillebon, Manchester, Mass.; Irving Kalikow, Swampscott, Mass.; A. Ze'ev Hed, Nashua, N.H.

[73] Assignee: Implemed, Inc., Brookline, Mass.

[21] Appl. No.: 777,090

[22] Filed: Oct. 16, 1991

[51] Int. Cl.$^5$ .............................................. A61B 17/32
[52] U.S. Cl. ...................................... 606/170; 128/4; 606/205
[58] Field of Search ............... 606/133, 205, 138, 206, 606/207, 208, 209, 210, 211, 174, 170; 30/191, 192, 250, 252, 341, 235, 211, 199, 177, 245; 128/4, 20; 294/19.1

[56] References Cited

U.S. PATENT DOCUMENTS

| | | |
|---|---|---|
| 848,126 | 3/1907 | Roosevelt . |
| 2,011,169 | 4/1932 | Wappler . |
| 2,114,695 | 4/1938 | Anderson . |
| 2,137,710 | 12/1937 | Anderson . |
| 2,214,985 | 4/1938 | Bachmann . |
| 2,234,686 | 1/1940 | Walter . |
| 2,507,710 | 5/1950 | Grosso ........................ 606/208 X |
| 2,790,437 | 4/1957 | Moore ........................ 294/19.1 X |
| 3,742,957 | 7/1973 | White . |
| 3,865,113 | 2/1975 | Sharon et al. . |
| 3,895,636 | 7/1975 | Schmidt . |
| 3,899,829 | 8/1975 | Storm et al. . |
| 3,967,625 | 7/1976 | Yoon . |
| 4,192,313 | 3/1980 | Ogami . |
| 4,240,431 | 12/1980 | Komiya . |
| 4,249,533 | 2/1981 | Komiya . |
| 4,520,815 | 6/1985 | Marinoff . |
| 4,598,699 | 7/1986 | Garren et al. . |
| 4,632,110 | 12/1986 | Sanagi . |
| 4,760,840 | 8/1988 | Fournier, Jr. et al. . |
| 4,763,668 | 8/1988 | Macek et al. . |
| 4,763,669 | 8/1988 | Jaeger ........................... 606/174 |
| 4,872,456 | 10/1989 | Hasson . |
| 4,880,015 | 11/1989 | Nierman ......................... 30/199 X |
| 4,944,093 | 7/1990 | Falk ............................... 606/205 X |
| 4,944,741 | 7/1990 | Hasson . |
| 4,945,920 | 8/1990 | Clossick . |
| 4,950,273 | 8/1990 | Briggs . |
| 5,002,543 | 3/1991 | Bradshal et al. . |
| 5,171,257 | 12/1992 | Ferzli ............................. 606/205 |

FOREIGN PATENT DOCUMENTS 0306123 3/1989 European Pat. Off. .
1430639 1/1966 France .
8911827 12/1989 World Int. Prop. O. .

OTHER PUBLICATIONS

"Endoscopy-The Real Cutting Edge," Health Science Section of The Boston Globe, Oct. 28, 1991 pp. 25-26.
Weck Endoscopy, section of product information brochures of Weck, A Squibb Company.
"A Direct Path To Diagnostic and Operative Control," section of product information brochures of Weck, A Squibb Company.

Primary Examiner—Richard J. Apley
Assistant Examiner—Karen Jalbert
Attorney, Agent, or Firm—Lahive & Cockfield

[57] ABSTRACT

A surgical tool for operating within a body cavity through a small diameter opening includes a substantially rigid member which is elongated along a first axis and which has a cross-sectional dimension to fit within the opening. A head is mounted on one end of the rigid member for movement in at least one plane through an angle with respect to the first axis. An operable control member is mounted on an opposite end of the rigid member for having at least one degree of manipulability. The control member is coupled to the head member through the rigid member such that manipulation of the control member through an angle with respect to the first axis causes movement of the head member through a corresponding angle. Accordingly, the head member can be steered within a body cavity by control external to the body cavity. In some embodiments, the control member is manipulable to a second degree for actuating an actuating member mounted on the head.

25 Claims, 5 Drawing Sheets

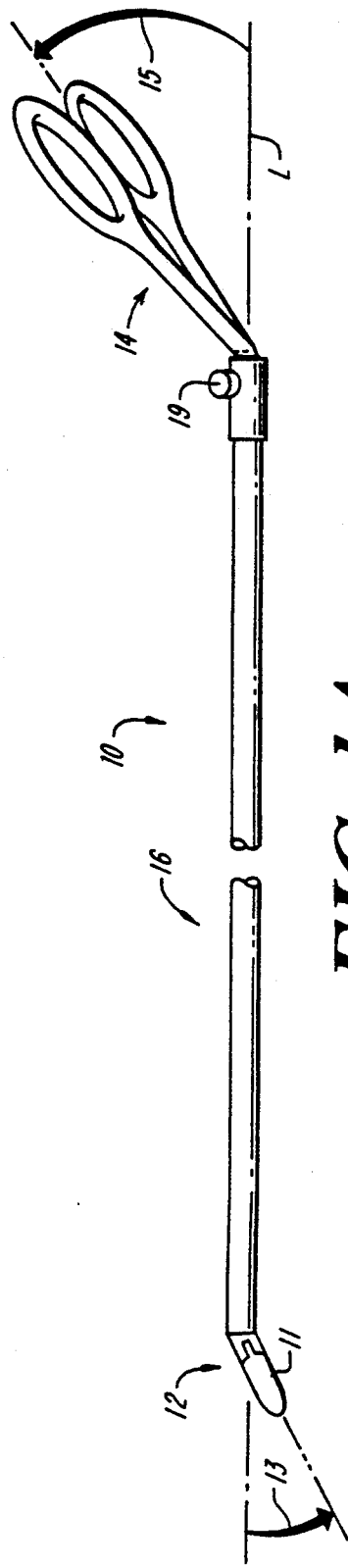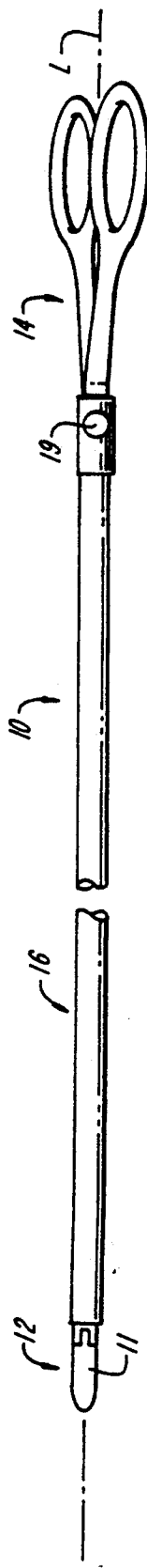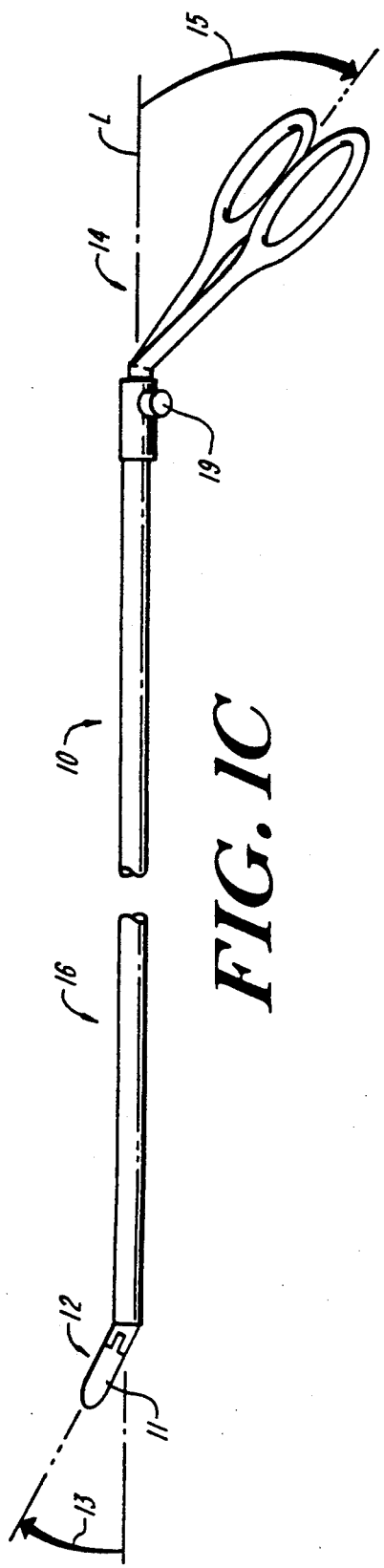

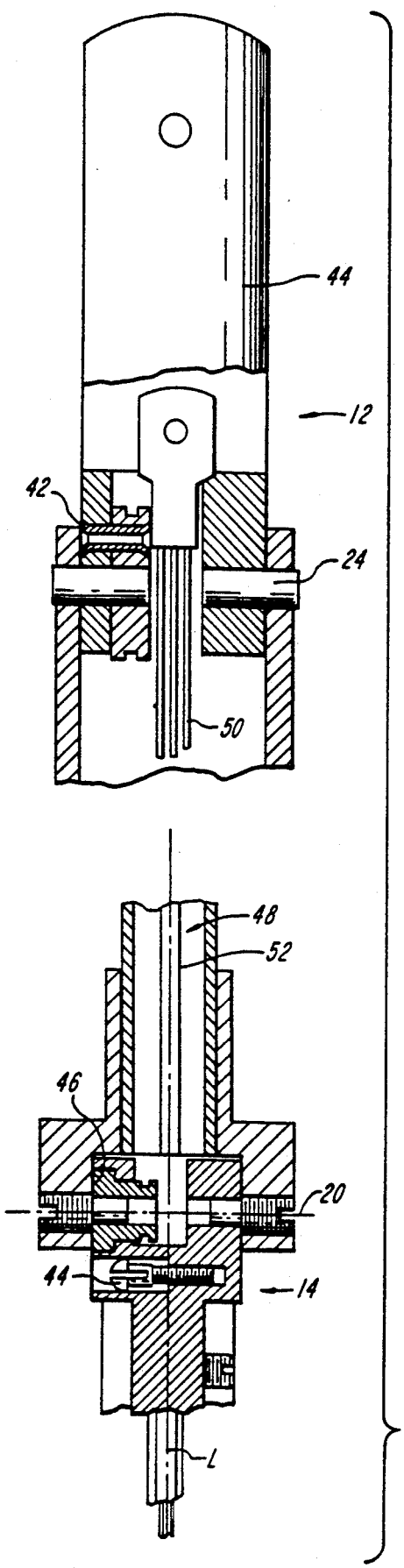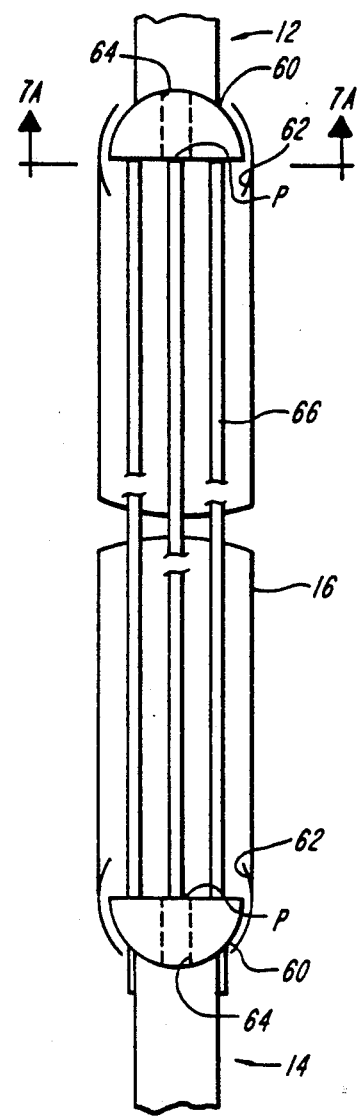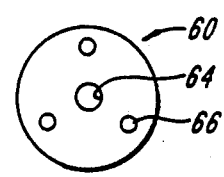
FIG. 6
FIG. 7
FIG. 7A

GENERIC ENDOSCOPIC INSTRUMENT

BACKGROUND OF THE INVENTION

The invention relates generally to the field of surgical instruments and, in particular, to an endoscopic instrument having at one end a headpiece that can be manipulated from an opposite end.

Endoscopic surgery involves accessing a patient's organs through a discrete opening. For example, laparoscopic surgery, which is a species of endoscopic surgery, involves accessing a patient's peritoneal cavity by way of an endoscope passing through the patient's abdominal wall. Other endoscopic techniques include bronchoscopy, colonoscopy, and esophagoscopy.

Depending on the specific endoscopic technique employed, the discrete opening providing access to the patient's organs may either be surgically created or naturally occurring. For example, in the case of laparoscopy an opening is surgically created in the patient's abdominal wall. On the other hand, in the case of peroral endoscopy, an endoscope is passed through a patient's mouth. In either case, the advantage of endoscopic surgery is found in providing access to the patient's organs without the need for a long incision and its attendant complications.

Endoscopes provide a conduit for the passage into a patient of various surgical instruments such as, for example, forceps, lasers, stents, and cameras. But, since endoscopes typically have small diameters to minimize the complications associated with introducing them into a patient, they limit the size of the instrument that can be passed through them.

Another problem associated with known endoscopic techniques is that of a surgeon not being able to manipulate adequately the internally disposed end of the endoscopic instrument. Accordingly, a surgeon using known endoscopic instruments is limited to accessing in a patient only the small area aligned with the endoscope's longitudinal access. In many applications, however, it is desirable for the surgeon to work in an area of the patient which is angularly offset from the endoscope's axis. With known endoscopic techniques, this can only be achieved by manipulating the entire endoscope.

It is, therefore, an object of the invention to provide a surgical tool for operating within a body cavity through a small diameter opening.

It is another object of the invention to provide such an instrument, the internally disposed end of which can be manipulated from outside of the body cavity.

SUMMARY OF THE INVENTION

These and other objects are achieved by the present invention which features a surgical tool for operating within a body cavity through a discrete opening. The tool has the advantage that its operable end is articulated so as to be manipulatable from outside of the body cavity.

The tool features a substantially rigid member which is elongate along a longitudinal axis. The member has a cross sectional diameter smaller than the discrete opening. A head is mounted on a forward end of the rigid member with articulation in at least one plane through an angle with respect to the longitudinal axis. In one embodiment of the invention, an actuable operating device is fixed to the head. The actuable operating device may be forceps, tongs, a hook, a stent, or the like.

It may also be desirable to mount non-actuable devices such as optical lighting fibres and a camera on the head.

The invention further features an operable control member mounted on a rearward end of the rigid member opposite the head. The control member has at least one degree of articulation for manipulating the head. Accordingly, the control member is coupled to the head through the rigid member so that movement of the control member through an angle with respect to the first axis causes movement of the head through a corresponding angle. The angles may correspond at a one to one ratio but may also correspond at other ratios such as two to one. As a result, the head can be steered by manual control outside of the body cavity.

In one embodiment of the invention, the coupling mechanism between the control member and head is a rigid rod. The coupling rod is pivotably connected to both the control member and the head, each of which rotates about an axis spaced apart from the coupling rod pivot connection. In this manner, manipulation of the control member about its rotational axis causes longitudinal displacement of the coupling rod which in turn causes corresponding rotational displacement of the head.

In another embodiment of the invention, the coupling mechanism between the control member and the head is a cable and pulley arrangement. The two ends of the cable are secured to the control member. The central portion of the cable engages a pulley fixed to the head. Typically, the cable is spot welded to the pulley so that longitudinal displacement of the cable causes rotational displacement of the pulley and, hence, rotational displacement of the head. Other techniques for engaging the cable and the pulley will be readily apparent. For example, the cable and pulley could be formed to resemble a chain and sprocket.

In some embodiments of the invention, the angular movement of the head takes place in the same plane as the angular movement of the control member. Additionally, in some embodiments, the control member and head move in opposite directions. In other embodiments, however, the direction of movement of the control member and the head are the same.

In embodiments of the invention including an actuable operating device fixed to the head, the control member includes a second degree of manipulability and is coupled to the actuable member for actuating it. The coupling can either be flexible along its entire length or comprise flexible ends connected by a rigid member. In this manner, the flexible ends of the coupling conform to angular movement of the head and control member so that angular displacement of the head and control member does not affect the actuation of the actuable operating device.

These and other features of the invention will be more fully appreciated by reference to the following detailed description, which is to be read in conjunction with the attached drawings in which like reference numbers refer to like elements throughout the several views.

BRIEF DESCRIPTION OF THE DRAWINGS

FIGS. 1A through 1C are schematic representations of an endoscopic surgical tool constructed in accordance with the teachings of the present invention, FIG. 6 is a partial section view taken along line 6—6 of FIG. 5, and FIGS. 7 and 7A are schematic views of still another embodiment of the tool depicted in FIG. 1.

DETAILED DESCRIPTION

Figure 2:
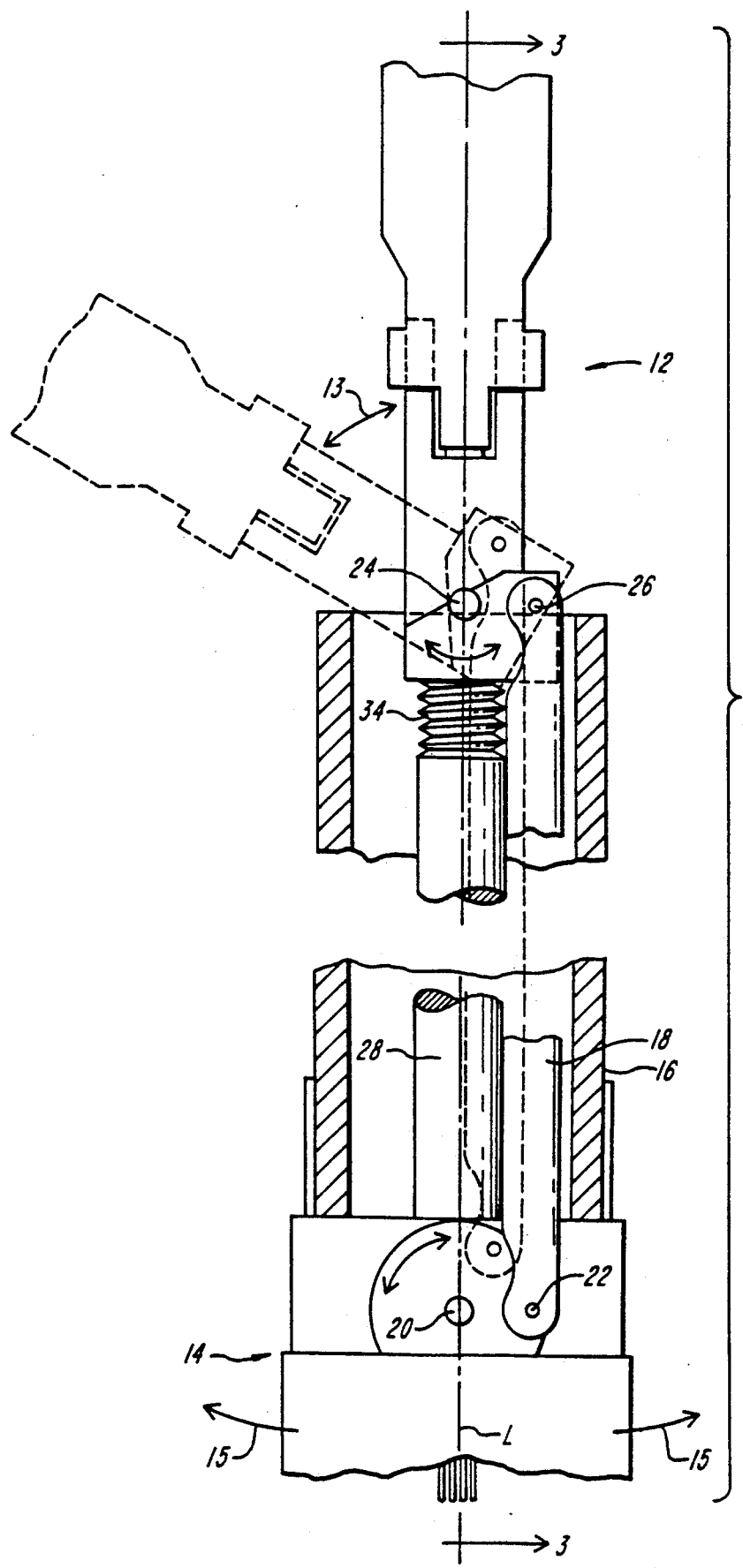
FIG. 2 is a more detailed, partial section view, of one embodiment of the tool depicted in FIG. 1.

In one aspect, the invention features a surgical tool for operating within a body cavity through a discrete opening while being manipulated from outside of the body. The tool has the advantage that the headpiece can be manipulated or steered from outside of the body to move through a plane and at an angle to the tool's entry path.

A tool 10 constructed in accordance with the teachings of the invention is shown in FIG. 1 which is a generally schematic view. The tool 10 is a generic endoscopic instrument meaning that it is suitable for use in conjunction with any form of endoscopic surgery wherein access to a patient's internal organs is provided through a discrete opening which is either surgically created or naturally occurring. The tool is intended to be utilized by being introduced to the interior of a patient through an endoscope or other form of relatively small diameter sheath. It has been found that the invention is particularly well suited for use in laparoscopic surgery.

Broadly, the instrument 10 includes three main sections, a head 12, a control member 14, and an elongated rigid member 16 extending therebetween. As will be described in greater detail herein below, the rigid member 16 is hollow. During endoscopy, laparoscopic or otherwise, the head 12 is disposed internally of the patient while the control member 14 is located outside of the patient for manipulation by a surgeon. To introduce the head 12 into the interior of the patient, an endoscope (not shown) is utilized in a known fashion to provide a discrete opening. So, for example, in laparoscopic surgery, an endoscope is passed through a patient's abdominal wall to provide access to the patient's peritoneal cavity. The tool 10 is then passed through the endoscope to position the head 12 internally of the patient. For purposes of illustration, forceps 11 are shown mounted on the head 12. As previously mentioned, however, various surgical instruments, actuable and non-actuable, can be utilized. For embodiments of the invention utilizing surgical instruments requiring an energy supply, such as laser knives, electric or laser cauterizing apparatus, and fiber optics, connection 19 is provided. Depending on the type of instrument mounted on the head 12, the connection 19 can be located either perpendicularly to the longitudinal axis L, as shown in the FIGURE, or parallel thereto. For example, when the instrument is a laser powered device, to simplify the coupling of laser energy from the connection 19 to the head 12, the connection will typically be oriented parallelly to the longitudinal axis L.

As shown in the FIGURE, the control member 14 has at least one degree of manipulability as indicated by arrows 15. That is, the control member 14 can be manipulated so as to be angularly offset from the rigid member's longitudinal axis L. Similarly, the head 12 can be angularly offset from the longitudinal axis L as indicated by arrows 13. In the illustrated embodiment of the invention, when the control member 14 is manipulated to be angularly offset from the longitudinal axis L, the head 12 is oppositely but correspondingly angularly offset. That is, for example, a 45° offset of the control member 14 causes a 45° offset of the head 12. As discussed in greater detail below, however, the tool 10 can be constructed so that the angular offsets of the control member 14 and the head 12, while corresponding, are not equal. Also, in the illustrated embodiments the control member 14 and the head 12 travel in the same plane. Again, however, the tool 10 can be constructed, so that they travel in different planes.

FIG. 2 is a partial section view of one embodiment of the invention wherein a rigid coupling member 18 couples the control member 14 to the head 12. The coupling member 18 is pivotably connected to the control member 14 at a coupling pivot 22 and to the head 12 at a coupling pivot 26. The control member itself is rotatable about an axis 20 and the head is rotatable about an axis 24. It is significant that the coupling pivots 22 and 26 are displaced from the control member rotational axis 20 and the head rotational axis 24 respectively. As a result, it can be seen that manipulating the control member 14 so that it becomes angularly offset from the longitudinal axis L causes longitudinal displacement of the rigid coupling member 18. This longitudinal displacement is translated by the coupling pivot 26 to rotational displacement of the head 12 about the head rotational axis 24. Accordingly, angular displacement of the control member 14 results in corresponding angular displacement of the head 12.

If the distance which the coupling pivot 22 is offset from the rotational axis 20 is equal to the distance which the coupling pivot 26 is offset from the rotational axis 24, the angular displacement of the control member 14 and the head 12 will be equal. If however, the coupling pivots 22 and 26 are offset different distances from their respective rotational axes 20 and 24, the angular displacements of the control member 14 and head 12 will not be equal. Depending on the requirements of specific applications, therefore, the geometry of the coupling pivots 22 and 26 and rotational axes 20 and 24 can be selected accordingly. For example, if the distance from coupling pivot 22 to rotational axis 20 is greater than the distance from coupling pivot 26 to the rotational axis 24, a specified degree of angular offset of the control member 14 will result in a greater degree of angular offset of the head 12. Of course, the opposite is true as well. As a result, the invention provides a surgical tool that can specifically be constructed to suit a given surgical application as well as a surgeon's personal preference.

Additionally, while the illustrated embodiment of the invention shows a tool wherein angular manipulation of the control member 14 causes opposed angular movement of the head 12, the tool 12 can be constructed so that the control member 14 and the head 12 move in the same direction. This can be achieved, for example, in the following manner.

As illustrated, when the member 14 and head 12 are aligned with longitudinal axis L, coupling pivots 22 and 26 are located at three o'clock in relation to rotational axes 20 and 24 respectively. If, however, the tool 10 were constructed so that, when the head 12 and control member 14 are axially aligned, the coupling pivot 22 is, at three o'clock and the coupling pivot 26 is at nine o'clock, rotational manipulation of the control member 14 would cause articulation of the head 12 in the same direction.

Figure 3:
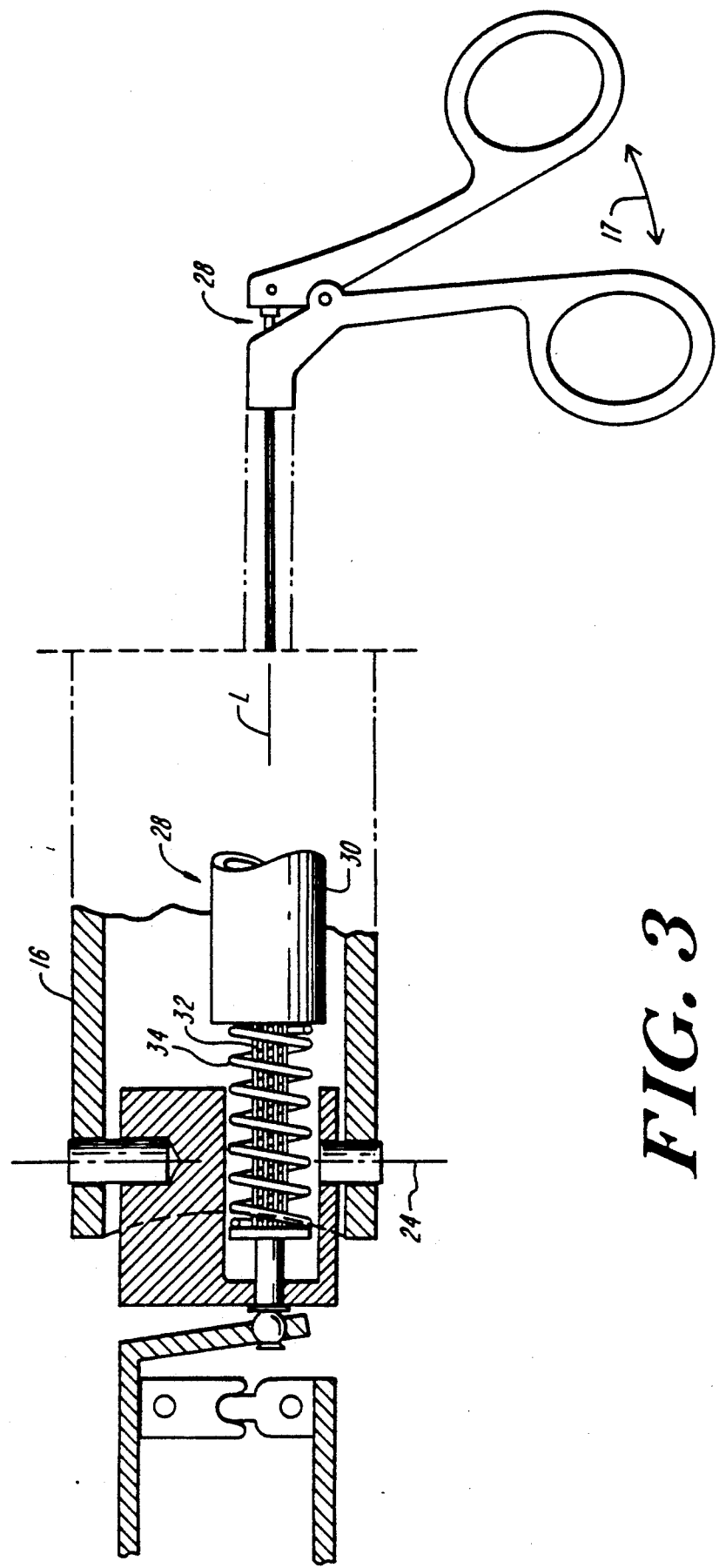
FIG. 3 is a partial section view taken along line 3—3 of FIG. 2, FIG. 4A–4C are schematic views of various non-actuable operating devices for mounting on the tool shown in FIG. 1.
Figure 4A:
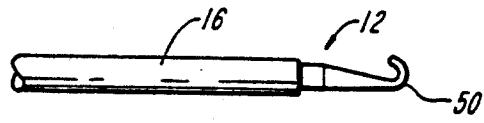
Figure 4B:
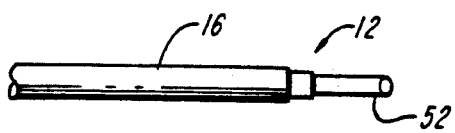
Figure 4C:
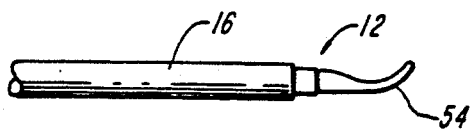

As shown in FIGS. 2 and 3, another coupling mechanism 28 runs generally parallel to the coupling member 18 within the rigid member 16. This coupling mechanism 28 is for embodiments of the invention wherein the control member 14 has a second degree of manipulability for actuating an actuable operating device such as forceps 11, mounted on the head 12. In embodiments of the invention, as illustrated in FIGS. 4A through 4C, wherein the head 12 carries an instrument that does not require actuation, such as, for example, a hook tip 50, fiber optic lasers 52, a curved spatula electrode 54 for either coagulation or cauterization, and the like, the control member 14 need only have one degree of manipulability.

In any event, the illustrated coupling mechanism 28 is more clearly visible in FIG. 3 wherein it is shown that the coupling mechanism 28 includes a rigid tube 30 from the front of which runs a group of small diameter cables 32. A spring 34 is also fixed to the front of the tube 30 and a connecting element 36 is fixed to the end of the spring 34. In this manner, longitudinal movement of the spring 34 and cables 32 is transmitted via the connecting element 36 to the actuating member on the head 12.

To actuate the actuating member, the control member 14 is manipulated as indicated by arrows 17. This causes longitudinal displacement of the coupling member 28 either toward or away from the head 12. In the case of the coupling element being moved toward the head 12, the spring becomes compressed thereby exerting a pushing force on the connecting element 36. In the case of the coupling element 28 being moved away from the head 12, the cables 32 exert a pulling force on the connecting element 36. Accordingly, manipulation of the control member 14 results in actuation in a known fashion of an actuating member located on the head 12.

It is a significant feature of the invention that the coupling element 28 includes the illustrated group of cables 32 and that the cables 32 are exposed at that portion of the coupling element 28 located adjacent the rotational axis 24. There is also a flexible connection (not shown) between the tube 30 and the control member 14 adjacent the rotational axis 20. As a result, when the control member 14 is manipulated to be angularly offset from the longitudinal axis L, thereby causing a corresponding angular articulation of the head 12, the cables 32 and the connection will flex. This enables articulation of the control member 14 and the head 12 and prevents inadvertent actuation of the actuable operating device. Were the coupling element 28 entirely rigid, on the other hand, articulation of the head 12 and control member 14 would be inhibited and inadvertent actuation would occur.

Figure 5:
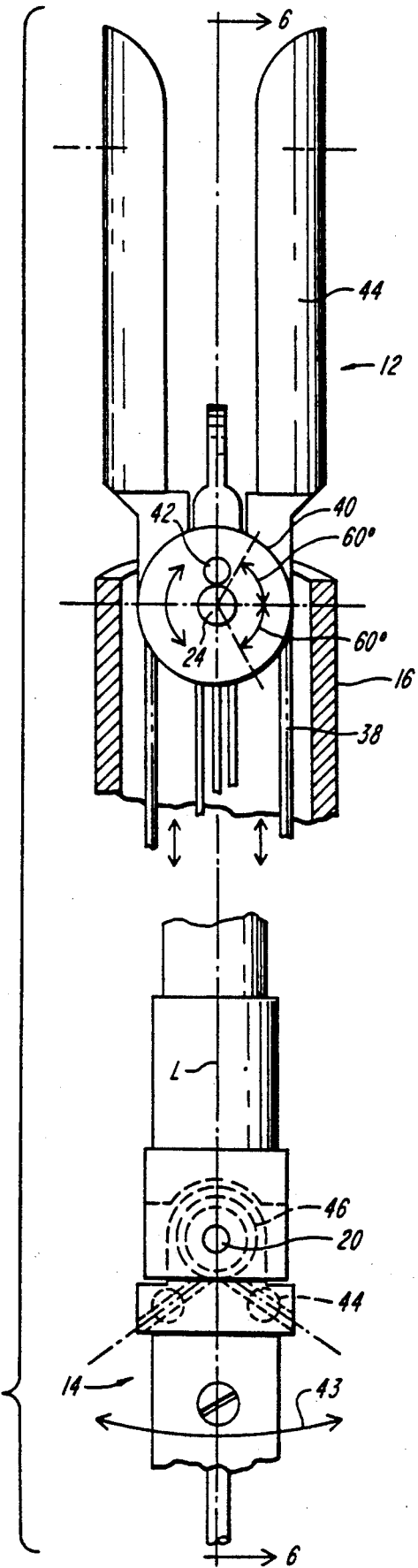
FIG. 5 is a detailed, partial section view, of another embodiment of the tool depicted in FIG. 1.

Another embodiment of the invention is shown in FIGS. 5 and 6 wherein rather than by the rigid coupling element 18, angular displacement of the control member is transmitted to the head 12 via a cable 38 and a pulley 40. The cable 38 is fixed to the pulley 40 such as by, for example, spot welding, so that movement of the cable 38 causes rotational movement of the pulley 40. The pulley 40, in turn, is fixed to the head 12 by a screw 42 and the cable 38 is secured to the control member 14 by screws 44. So, as illustrated, displacement of the control member 14, as indicated by arrows 43, results in the cable 38 causing rotational movement of the pulley 40 which is transmitted to the head 12 by the screw 42.

As shown in phantom, the cable 38 is guided around a hub 46 before being secured by the screws 44. The provides proper spacing of the cable 38 as it passes through the rigid member 16. Also, the screws 44 can be turned to selectively position the control member 14 with respect to the head 12 and to adjust the tension along the cable 38. While in the illustrated embodiment the cable 38 travels through the rigid member 16 generally parallel to the longitudinal axis L, the cable 38 could be arranged in a crossing pattern. In such a case, the head 12 would articulate in the same direction as the control member 14.

Similarly to the embodiment depicted in FIGS. 2 and 3, the embodiment of the invention shown in FIGS. 5 and 6 includes another coupling element 48 for actuating an actuating member located on the head 12. The coupling element 48 includes a group of cables 50 passing through a fixed guide tube 52. Again, the cables are exposed adjacent the pivot axes of the control member 14 and the head 12 to both afford articulability to these elements and to prevent inadvertent actuation during steering. The cables are "semi-rigid" in that while necessarily being flexible enough to bend during angular manipulation, the cables 50 must be rigid enough so that when they are longitudinally displaced toward the head 12 they exert a pushing force to effect actuation of an actuable operating device such as the tongs 44 shown. It has been found that a bundle made of four strands of spring steel each of diameter 0.5 mm and spot welded together at one or both ends is suitable for this purpose.

In still another embodiment of the invention, as shown in FIG. 7, the head 12 and control member 14 are mounted to the rigid member 16 so that they can pivot about a point P. This provides this embodiment of the invention with the ability to manipulate the control member 14, and thereby the head 12, in multiple planes. A hemisphere 60 fits in a socket 62 defined by the elongated rigid member 16. The hemisphere 60 includes a hole 64 to allow a coupling element, like coupling elements 28 and 48 discussed above, to pass from the control member 19 to the head 12 in order to couple the head 12 and control member 14 together. In this embodiment of the invention like hemispheres 60 are located at opposite ends of the rigid member 16. Steering rods 66 transmit displacement of the hemisphere 60 at the control member end of the rigid member 16 to the hemisphere 60 located at the opposite end of the rigid member 16. The arrangement of the steering rods 64 is shown in FIG. 7A which is a view taken along line A—A of FIG. 7.

As stated, the advantage of this embodiment of the invention is that by mounting each of the control member 14 and the head 12 to the rigid member 16 via this ball and socket arrangement, non-planar movement can be transmitted from the control member 14 to the head 12.

While various features and embodiments of the invention have been described in detail, it should be understood that other alterations will be apparent to those skilled in the art and are intended to be embraced within the spirit and scope of the invention. The invention is to be defined, therefore, not by the preceding description but by the claims that follow.

What is claimed is:

1. A surgical tool for operating within a body cavity through a small diameter opening while being manipulated from outside the body cavity comprising a substantially rigid member, having a proximal end and a distal end, being elongated along a longitudinal axis and having a cross sectional dimension to fit within said opening, a head member mounted on and extending axially from, the distal end of said rigid member for movement in at least one plane through an angle with respect to said longitudinal axis, an operable control member mounted extending axially from the proximal end of said elongated member for having a first degree of manipulability and coupled to said head member through said rigid member such that manipulation of said control member through an angle with respect to said longitudinal axis causes movement of said head member through a corresponding angle whereby said head member can be steered within a body cavity by control external to said body cavity, and an actuable operating device fixed to said head member, said operable control member having a second degree of manipulability for actuating said actuable operating device, said control member being independently coupled to said actuable operating device at said head through said rigid member for actuation of said actuable operating device which is unrestricted and unaffected by manipulation of said control member in said first degree of manipulation of said control member in said first degree of manipulability.

2. A tool as set forth in claim 1 wherein each of said head and said operable control member is mounted to said rigid member for pivoting about a point located on said longitudinal axis.

3. A tool as set forth in claim 1 wherein each of said head and said operable control member is mounted to said rigid member for rotating about a rotational axis perpendicular to said longitudinal axis.

4. A tool in accordance with claim 1 wherein the angular movement of said head is in a different plane from the angular movement of said operable control member.

5. A tool in accordance with claim 1 wherein the angular degrees of movement of said control member is the same as the angular degrees of movement of said head.

6. A tool in accordance with claim 1 wherein the direction of movement of said control member is opposed to the direction of movement of said head.

7. A tool in accordance with claim 1 wherein said coupling between said control member and said actuable operating device in said head is at least partially a flexible coupling.

8. A tool in accordance with claim 7 wherein said coupling includes a flexible member at both said control member end and at said head connected by a rigid guide tube between them enclosed within said rigid member wherein said flexible members conform to angular movement of said head and said control member without affecting the actuation of said actuable operating device.

9. A tool in accordance with claim 1 wherein said actuable operating device is a tongs device.

10. A tool in accordance with claim 1 wherein said actuable operating device is a forceps device.

11. A surgical tool for operating within a body cavity through a small diameter opening while being manipulated from outside the body cavity comprising a substantially rigid member being elongated along a longitudinal axis and having a cross sectional dimension to fit within said opening, a head mounted on the end of said rigid member for movement in at least one plane through an angle with respect to said longitudinal axis, an actuable operating device mounted on said head for being actuated within the body cavity, an operable control member connected to the end of said rigid member opposite said head member for having at least two degrees of manipulability, said control member being coupled to said head member and said actuable operating device through said rigid member whereby manipulation of said control member in a first degree of manipulability causes said movement of said head member; and means, extending through said rigid member, for independently coupling said control member to said actuable operating device whereby manipulation of said control member in a second degree of manipulability causes said actuation of said actuable operating device which is unrestricted and unaffected by manipulation of said control member in said first degree of manipulability.

12. A tool as set forth in claim 11 wherein each of said head and said control member is mounted on said rigid member for pivoting about a point located on said longitudinal axis.

13. A tool as set forth in claim 12 wherein said movement of said head includes rotation about a first rotational axis and said first degree of manipulability of said control member includes rotation about a second rotational axis.

14. A tool as set forth in claim 13 further comprising
an elongate rigid coupling member extending through said rigid member, said rigid coupling member being pivotably connected at a first end to said head and at a second end to said control member, said first end pivotable connection being spaced apart from said first rotational axis and said second end pivotable connection being spaced apart from said second rotational axis, whereby manipulation of said control member in said first degree causes said rotation of said head member.

15. A tool as set forth in claim 13 further comprising
a pulley fixed to said head,
a cable secured at its ends to said control member and at a position between its ends to said pulley, whereby manipulation of said control member in said first degree causes longitudinal displacement of said cable which causes rotational displacement of said head about said first rotational axis.

16. A surgical tool as set forth in claim 13 wherein said means for coupling said control member to said actuable control device comprises
a hollow, fixed, guide tube, and
a group of semi-flexible cables passing through said guide tube, said cables being exposed from said guide tube at locations adjacent said first and second rotational axes.

17. A surgical tool as set forth in claim 11 wherein said means for coupling said control member to said actuable control device comprises
a tube,
a spring between said tube and said actuable member for exerting a pushing force on said actuable member when said tube is moved toward said head, and a group of cables passing through said spring and connected to said tube and coupled to said actuable member for exerting a pulling force on said actuable member when said tube is moved toward said control member.

18. A tool as set forth in claims 11 wherein the angular movement of said head is in the same plane as the angular movement of said operable control member.

19. A tool as set forth in claim 18 wherein the angular degrees of movement of said control member is the same as the angular degrees of movement of said head.

20. A tool as set forth in claim 11 wherein the direction of movement of said control member is opposed to the direction of movement of said head.

21. A tool as set forth in claim 11 wherein said actuable operating device is a tongs device.

22. A tool as set forth in claim 11 wherein said actuable operating device is a forceps device.

23. A tool as set forth in claim 11 wherein each of said head and said operable control member is mounted to said rigid member for rotating about a rotational axis perpendicular to said longitudinal axis.

24. A tool in accordance with claim 11 wherein the angular movement of said head is in a different plane from the angular movement of said operable control member.

25. A tool in accordance with claim 11 wherein the angular degrees of movement of said control member is the same as the angular degrees of movement of said head.

* * * * *